(12) United States Patent
Weitz et al.

(10) Patent No.: US 10,258,987 B2
(45) Date of Patent: Apr. 16, 2019

(54) FLUID INFECTION USING ACOUSTIC WAVES

(71) Applicants: President and Fellows of Harvard College, Cambridge, MA (US); The University Court of the University of Glasgow, Glasgow (GB)

(72) Inventors: David A. Weitz, Bolton, MA (US); Thomas Franke, Augsburg (DE)

(73) Assignees: President and Fellows of Harvard College, Cambridge, MA (US); The University Court of the University of Glasgow, Glasgow (GB)

( * ) Notice: Subject to any disclaimer, the term of this patent is extended or adjusted under 35 U.S.C. 154(b) by 154 days.

(21) Appl. No.: 15/320,408

(22) PCT Filed: Jun. 25, 2015

(86) PCT No.: PCT/US2015/037662
§ 371 (c)(1),
(2) Date: Dec. 20, 2016

(87) PCT Pub. No.: WO2015/200616
PCT Pub. Date: Dec. 30, 2015

(65) Prior Publication Data
US 2017/0246634 A1    Aug. 31, 2017

Related U.S. Application Data

(60) Provisional application No. 62/017,301, filed on Jun. 26, 2014.

(51) Int. Cl.
*B01L 3/00* (2006.01)
*B01F 13/00* (2006.01)
(Continued)

(52) U.S. Cl.
CPC ...... *B01L 3/502784* (2013.01); *B01F 3/0819* (2013.01); *B01F 5/0471* (2013.01);
(Continued)

(58) Field of Classification Search
CPC .............. B01F 13/0071; B01F 15/0241; B01F 15/0263; B01F 2215/0037;
(Continued)

(56) References Cited

U.S. PATENT DOCUMENTS 5,512,131 A    4/1996  Kumr et al.
5,688,405 A    11/1997 Dickinson et al.
(Continued)

FOREIGN PATENT DOCUMENTS

CN    101099727 A    1/2008
EP    1398025 A1     3/2004
(Continued)

OTHER PUBLICATIONS

U.S. Appl. No. 60/392,195, filed Jun. 28, 2002, Stone et al.
(Continued)

*Primary Examiner* — Jennifer Wecker
(74) *Attorney, Agent, or Firm* — Wolf, Greenfield & Sacks, P.C.

(57) ABSTRACT

The present invention generally relates to the manipulation of fluids using acoustic waves such as surface acoustic waves. In some aspects, one fluid may be introduced into another fluid via application of suitable acoustic waves. For example, a fluid may be added or injected into another fluid by applying acoustic waves where, in the absence of the acoustic waves, the fluid cannot be added or injected, e.g., due to the interface or surface tension between the fluids. Thus, for example, a fluid may be injected into a droplet of another fluid. Other embodiments of the invention are generally directed to systems and methods for making or using such systems, kits involving such systems, or the like.

20 Claims, 2 Drawing Sheets

(51) Int. Cl.

| | | |
|---|---|---|
| *B01F 3/08* | (2006.01) | |
| *B01J 19/00* | (2006.01) | |
| *B01F 15/02* | (2006.01) | |
| *B01F 5/04* | (2006.01) | |
| *C12M 1/00* | (2006.01) | |
| *G01N 15/10* | (2006.01) | |
| *C12N 15/82* | (2006.01) | |
| *C07K 14/415* | (2006.01) | |

(52) U.S. Cl.
CPC ...... *B01F 13/0071* (2013.01); *B01F 15/0241* (2013.01); *B01F 15/0263* (2013.01); *B01J 19/0093* (2013.01); *B01L 3/502776* (2013.01); *B01F 2215/0037* (2013.01); *B01F 2215/0463* (2013.01); *B01J 2219/00792* (2013.01); *B01J 2219/00833* (2013.01); *B01J 2219/00932* (2013.01); *B01L 2200/0647* (2013.01); *B01L 2200/16* (2013.01); *B01L 2300/0816* (2013.01); *B01L 2300/0867* (2013.01); *B01L 2400/0436* (2013.01); *B01L 2400/0439* (2013.01); *B01L 2400/0487* (2013.01); *C07K 14/415* (2013.01); *C12N 15/8222* (2013.01); *C12N 15/8243* (2013.01); *C12N 15/8261* (2013.01); *Y02A 40/146* (2018.01)

(58) Field of Classification Search
CPC ............ B01F 2215/0463; B01F 3/0819; B01F 5/0471; B01J 19/0093; B01J 2219/00792; B01J 2219/00833; B01J 2219/00932; B01L 2200/0647; B01L 2200/16; B01L 2300/0816; B01L 2300/0867; B01L 2400/0436; B01L 2400/0439; B01L 2400/0487; B01L 3/502776; B01L 3/502784; C07K 14/415; C12N 15/8222; C12N 15/8243; C12N 15/8261; Y02A 40/146

See application file for complete search history.

(56) References Cited

U.S. PATENT DOCUMENTS

| | | | |
|---|---|---|---|
| 6,355,198 | B1 | 3/2002 | Kim et al. |
| 6,777,245 | B2 | 8/2004 | Wixforth |
| 7,708,949 | B2 | 5/2010 | Stone et al. |
| 7,942,568 | B1 | 5/2011 | Branch et al. |
| 8,573,060 | B2 | 11/2013 | Huang et al. |
| 8,765,485 | B2 | 7/2014 | Link et al. |
| 9,038,919 | B2 | 5/2015 | Link et al. |
| 9,695,390 | B2 | 7/2017 | Weitz et al. |
| 2001/0055529 | A1 | 12/2001 | Wixforth |
| 2002/0009015 | A1 | 1/2002 | Laugharn et al. |
| 2004/0069717 | A1 | 4/2004 | Laurell et al. |
| 2005/0172476 | A1 | 8/2005 | Stone et al. |
| 2006/0163385 | A1 | 7/2006 | Link et al. |
| 2007/0003442 | A1 | 1/2007 | Link et al. |
| 2007/0125941 | A1 | 6/2007 | Lee et al. |
| 2007/0206055 | A1 | 9/2007 | Zapka et al. |
| 2009/0226994 | A1* | 9/2009 | Lemor ............... B01L 3/502715 435/173.1 |
| 2010/0139377 | A1* | 6/2010 | Huang ...................... C02F 1/76 73/61.75 |
| 2010/0200092 | A1 | 8/2010 | Beltram et al. |
| 2010/0248064 | A1 | 9/2010 | La O' et al. |
| 2011/0032528 | A1 | 2/2011 | Charette et al. |
| 2011/0127164 | A1 | 6/2011 | Sinha et al. |
| 2011/0275143 | A1 | 11/2011 | Prakash et al. |
| 2011/0277848 | A1 | 11/2011 | Burns et al. |
| 2012/0146457 | A1 | 6/2012 | Goto et al. |
| 2012/0149126 | A1 | 6/2012 | Wilson et al. |
| 2012/0160746 | A1 | 6/2012 | Thorslund |
| 2013/0192958 | A1 | 8/2013 | Ding et al. |
| 2013/0213488 | A1* | 8/2013 | Weitz ................... C12M 23/16 137/13 |
| 2013/0236901 | A1* | 9/2013 | Potier ................ G01N 35/1009 435/6.12 |
| 2014/0008307 | A1 | 1/2014 | Guldiken et al. |
| 2015/0192546 | A1 | 7/2015 | Weitz et al. |
| 2015/0298157 | A1 | 10/2015 | Weitz et al. |
| 2017/0321177 | A1 | 11/2017 | Weitz et al. |
| 2018/0257076 | A1 | 9/2018 | Weitz et al. |

FOREIGN PATENT DOCUMENTS

| | | | |
|---|---|---|---|
| EP | 1 905 427 | A1 | 4/2008 |
| EP | 2014280 | A1 | 1/2009 |
| GB | 2453534 | A | 4/2009 |
| JP | 7304997 | A | 11/1995 |
| JP | 2004161739 | A | 6/2004 |
| JP | 4472002 | B2 | 2/2010 |
| WO | WO 1996/29629 | A2 | 9/1996 |
| WO | WO 1998/06667 | A1 | 2/1998 |
| WO | WO 01/05731 | A1 | 1/2001 |
| WO | WO 2001/89787 | A2 | 11/2001 |
| WO | WO 2004/002627 | A2 | 1/2004 |
| WO | WO 2004/048356 | A1 | 6/2004 |
| WO | WO 2004/091763 | A2 | 10/2004 |
| WO | WO 2005/021151 | A1 | 3/2005 |
| WO | WO 2005/037267 | A1 | 4/2005 |
| WO | WO 2007/128045 | A1 | 11/2007 |
| WO | WO 2007/141002 | A1 | 12/2007 |
| WO | WO 2008/000042 | A1 | 1/2008 |
| WO | WO 2008/072155 | A1 | 6/2008 |
| WO | WO 2009/077147 | A2 | 6/2009 |
| WO | WO 2010/121328 | A1 | 10/2010 |
| WO | WO 2012/027366 | A2 | 3/2012 |
| WO | WO 2012/098140 | A1 | 7/2012 |
| WO | WO 2012/135259 | A1 | 10/2012 |
| WO | WO 2014/004630 | A1 | 1/2014 |
| WO | WO 2014/066624 | A1 | 5/2014 |

OTHER PUBLICATIONS

U.S. Appl. No. 60/424,042, filed Nov. 5, 2002, Link et al.
U.S. Appl. No. 60/461,954, filed Apr. 10, 2003, Link et al.
U.S. Appl. No. 60/498,091, filed Aug. 27, 2003, Link et al.
U.S. Appl. No. 60/659,045, filed Mar. 4, 2005, Weitz et al.
U.S. Appl. No. 60/659,046, filed Mar. 4, 2005, Garstecki et al.
U.S. Appl. No. 61/665,087, filed Jun. 27, 2012, Weitz et al.
U.S. Appl. No. 61/731,565, filed Nov. 30, 2012, Nicol et al.
U.S. Appl. No. 62/017,301, filed Jun. 26, 2014, Weitz et al.
Office Action dated Jun. 24, 2015 for U.S. Appl. No. 13/818,146.
Office Action dated Nov. 13, 2015 for U.S. Appl. No. 13/818,146.
Advisory Action dated May 11, 2016 for U.S. Appl. No. 13/818,146.
International Search Report and Written Opinion dated Apr. 10, 2012 for Application No. PCT/US2011/048804.
International Preliminary Report on Patentability dated Mar. 7, 2013 for Application No. PCT/US2011/048804.
Partial European Search Report dated Jul. 11, 2017 for Application No. EP 11820522.8.
International Search Report and Written Opinion dated Sep. 9, 2013 for Application No. PCT/US2013/047829.
International Preliminary Report on Patentability dated Jan. 8, 2015 for Application No. PCT/US2013/047829 dated Jan. 8, 2015.
International Search Report and Written Opinion dated Mar. 11, 2014 for Application No. PCT/US2013/066591.
International Preliminary Report on Patentability for Application No. PCT/US2013/066591 dated May 7, 2015.
International Search Report and Written Opinion dated Sep. 18, 2015 for Application No. PCT/US2015/037662.
International Preliminary Report on Patentability for Application No. PCT/US2015/037662 dated Jan. 5, 2017.
International Search Report and Written Opinion for Application No. PCT/US2016/048513 dated Nov. 4, 2016.
Abate et al., High-throughput injection with microfluidics using picoinjectors. Proc Natl Acad Sci U S A. Nov. 9, 2010;107(45):19163-6. doi: 10.1073/pnas.1006888107. Epub Oct. 20, 2010.

(56) References Cited

OTHER PUBLICATIONS

Collins et al., The particle valve: On-demand particle trapping, filtering, and release from a microfabricated polydimethylsiloxane membrane using surface acoustic waves. Applied Physics Letters. Jul. 2014;105:33509.

Franke et al., Surface acoustic wave (SAW) directed droplet flow in microfluidics for PDMS devices. Lab Chip. Sep. 21, 2009;9(18):2625-7.

Franke et al., Surface acoustic wave actuated cell sorting (SAWACS). Lab Chip. Mar. 21, 2010;10(6):789-94.

Ravula et al., A microfluidic system combining acoustic and dielectrophoretic particle preconcentration and focusing. Sensors and Actuators B: Chemical. 2008;130(2):645-52.

Schmid et al., Acoustic modulation of droplet size in a T-junction. Applied Physics Letters. Mar. 31, 2014;104(13):133501-4. DOI: 10.1063/1.4869536.

Schmid et al., Novel surface acoustic wave (SAW)-driven closed PDMS flow chamber. Microfluidics and Nanofluidics. Jan. 2012;12(1-4):229-35.

Schmid et al., SAW-controlled drop size for flow focusing. Lab Chip. May 7, 2013;13(9):1691-4. doi: 10.1039/c3lc41233d.

Shi et al., Focusing microparticles in a microfluidic channel with standing surface acoustic waves (SSAW). Lab Chip. Feb. 2008;8(2):221-3.

Skowronek et al., Particle deflection in a poly(dimethylsiloxane) microchannel using a propagating surface acoustic wave: size and frequency dependence. Anal. Chem., Sep. 2013, 85 (20), 9955-59.

Tsutsui et al., Cell Separation by Non-Inertial Force Fields in Microfluidic Systems. Mech Res Commun. Jan. 1, 2009;36(1):92-103.

Wood et al., Formation and manipulation of two-dimensional arrays of micron-scale particles in microfluidic systems by surface acoustic waves. Applied Physics Letters. 2009;94(5):054101.

Partial European Search Report for Application No. EP 11820522.8 dated Jul. 11, 2017.

Extended European Search Report for Application No. 11820522.8 dated Oct. 13, 2017.

International Preliminary Report on Patentability for Application No. PCT/US2016/048513 dated Mar. 8, 2018.

Office Action dated Sep. 17, 2018 for U.S. Appl. No. 15/604,085.

* cited by examiner

FLUID INFECTION USING ACOUSTIC WAVES

RELATED APPLICATIONS

This application is a national stage filing under 35 U.S.C. § 371 of International Application No. PCT/US2015/037662, filed Jun. 25, 2015, entitled "Fluid Injection Using Acoustic Waves," by David A. Weitz, et al., which claims the benefit of U.S. Provisional Patent Application Ser. No. 62/017,301, filed Jun. 26, 2014, entitled "Fluid Injection Using Acoustic Waves," by Weitz, et al., each of which is incorporated herein by reference in its entirety.

GOVERNMENT FUNDING

This invention was made with government support under Grant No. DMR-0820484 awarded by the National Science Foundation. The government has certain rights in the invention.

FIELD

The present invention generally relates to the manipulation of fluids using acoustic waves such as surface acoustic waves.

BACKGROUND

The manipulation of fluids to form fluid streams of desired configuration, discontinuous fluid streams, droplets, particles, dispersions, etc., for purposes of fluid delivery, product manufacture, analysis, and the like, is a relatively well-studied art. Examples of methods of producing droplets in a microfluidic system include the use of T-junctions or flow-focusing techniques. However, improvements in such techniques are still needed.

SUMMARY

The present invention generally relates to the manipulation of fluids using acoustic waves such as surface acoustic waves. The subject matter of the present invention involves, in some cases, interrelated products, alternative solutions to a particular problem, and/or a plurality of different uses of one or more systems and/or articles.

In one aspect, the present invention is generally directed to a method, such as a method for injection or introduction of fluids, e.g., into a droplet. In certain embodiments, acoustic waves such as surface acoustic waves are used.

In one set of embodiments, the method includes acts of providing a microfluidic system comprising a first microfluidic channel and a second microfluidic channel contacting the first microfluidic channel at a junction, providing a droplet of the first fluid contained by a carrying fluid in the first microfluidic channel, and a second fluid in the second microfluidic channel, wherein the first fluid and the second fluid contact each other at least partially within the junction to define a fluidic interface, and applying acoustic waves to the interface to urge the second fluid to flow into the droplet wherein, in the absence of the acoustic waves, the second fluid is not urged to enter the droplet.

The method, in accordance with another set of embodiments, includes acts of providing a microfluidic system comprising a first microfluidic channel and a second microfluidic channel contacting the first microfluidic channel at an intersection, providing a first fluid in the first microfluidic channel and a second fluid in the second microfluidic channel, wherein the first fluid and the second fluid contact each other at least partially within the intersection to define a fluidic interface, and applying acoustic waves to the interface to urge the second fluid to enter the first microfluidic channel, wherein, in the absence of the acoustic waves, the second fluid is not urged to pass through the intersection to enter the first microfluidic channel.

Yet another set of embodiments is generally directed to a method comprising laminarly flowing a first fluid and a second fluid in parallel within a microfluidic channel, and applying acoustic waves to an interface between the first fluid and the second fluid to cause at least some mixing of the first fluid and the second fluid.

According to still another set of embodiments, the method includes acts of providing a microfluidic system comprising a first fluid contacting a second fluid at an interface separating the first fluid and the second fluid, and applying acoustic waves to the interface, wherein the acoustic waves disrupt the interface to cause at least some mixing of the first fluid and the second fluid.

In another aspect, the present invention encompasses methods of making one or more of the embodiments described herein, for example, microfluidic devices comprising acoustic wave generators. In still another aspect, the present invention encompasses methods of using one or more of the embodiments described herein, for example, microfluidic devices comprising acoustic wave generators.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

The present invention generally relates to the manipulation of fluids using acoustic waves such as surface acoustic waves. In some aspects, one fluid may be introduced into another fluid via application of suitable acoustic waves. For example, a fluid may be added or injected into another fluid by applying acoustic waves where, in the absence of the acoustic waves, the fluid cannot be added or injected, e.g., due to the interface or surface tension between the fluids. Thus, for example, a fluid may be injected into a droplet of another fluid. Other embodiments of the invention are generally directed to systems and methods for making or using such systems, kits involving such systems, or the like.

Figure 1:
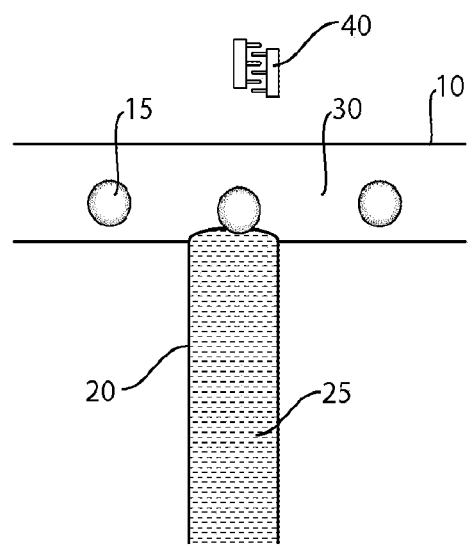
FIG. 1 illustrates fluid injection into droplets in accordance with one embodiment of the invention.

One embodiment of the invention for injecting a fluid into a droplet using acoustic waves is shown in FIG. 1. In this figure, microfluidic channel 10 contains a droplet 15 flowing from left to right. For example, droplet 15 may be substantially immiscible with a carrying fluid within channel 10, or droplet 15 may be a relatively hydrophilic fluid carried within a relatively hydrophobic fluid within channel 10 (or vice versa).

Intersecting microfluidic channel 10 at intersection 30 is microfluidic channel 20. Although shown here as an orthogonal intersection, it should be understood that in other embodiments, the intersection may occur at other angles as well, and/or that channel 10 may not necessarily be straight as it passes through the intersection. Within microfluidic channel 20 is a fluid 25 that is to be injected into droplet 10. Fluid 25 may the same or different from the fluid within droplet 15, and in some cases, fluid 25 may be substantially miscible with the fluid within droplet 15. In some cases, the fluids are partially or fully miscible to facilitate mixing.

Normally, in the absence of external forces, fluid 25 cannot enter droplet 15. Due to surface tension or other effects, even if fluid 25 comes into contact with droplet 15 at intersection 30, an interface is created that prevents any of the fluid from entering into droplet 15. The interface can be surprisingly strong on the microscale, preventing any mixing from occurring. Accordingly, without anything further, even though droplet 15 may come into contact with fluid 25, no mixing or injection of fluid 25 into droplet 15 can occur.

However, the interface may be disrupted in various ways to allow mixing to occur. For example, in one set of embodiments, acoustic waves can be applied to the interface (or to intersection 30) that can overcome the interface to allow at least some mixing or injection of fluid 25 into droplet 15. In some cases, the acoustic waves may affect the position of the interface, e.g., which may cause the interface to stretch or break to release fluid into the droplet, and/or the acoustic waves may apply energy to the interface which disrupts the interface in some fashion. In addition, the intensity and/or the duration of the acoustic waves can also be controlled, e.g., to control the amount of fluid entering the droplet. In some embodiments, the acoustic waves may be continuously or intermittently applied. In addition, in some cases, the acoustic waves may be used to control the relative pressures of the fluids flowing into and out of intersection 30. For instance, acoustic waves may be used to increase one or more inlet pressures, and/or to decrease the outlet pressure of the fluid exiting intersection 30.

In one set of embodiments, acoustic wave generators such as interdigitated transducers may be used to direct acoustic waves at the interface. For instance, as is shown in FIG. 1, interdigitated transducers 40 may be positioned so as to direct acoustic waves at the interface. The interdigitated transducers may be positioned next to the interface, or some distance away in some cases, as the acoustic waves may be transmitted towards the interface, e.g., through materials defining the microfluidic channels.

Figure 2:
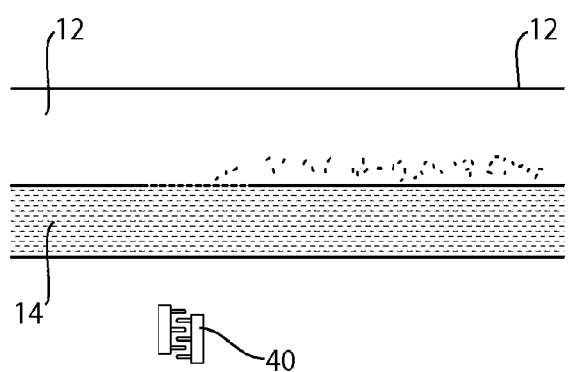
FIG. 2 illustrates fluid mixing at an interface, in another embodiment of the invention.

Another non-limiting example embodiment of the invention may be seen in FIG. 2, where two fluids 12, 14 laminarly flow side-by-side within microfluidic channel 10. The fluids may be substantially miscible or substantially immiscible, etc. Typically, under such conditions, very little mixing of fluids 12 and 14 may occur, e.g., due to the laminar flow. However, when acoustic waves are applied, e.g., via interdigitated transducers 40, at least a portion of the interface between fluids 12 and 14 may be disrupted, e.g., as discussed above, which may allow some mixing of fluids 12 and 14 to occur.

It should be noted that these examples are by way of illustration only. More generally, various aspects of the present invention are generally directed to systems and methods of injecting or mixing fluids, e.g., within channels such as microfluidic channels, by applying acoustic waves to a portion of the fluid. The acoustic waves may, in some cases, increase or decrease the pressure of the fluid, which may be used to cause mixing. The acoustic waves may be directed at any portion of any channel containing a fluid. Such control of fluid flow may be used in various ways, e.g., as discussed herein. In addition, in some embodiments, one or more acoustic wave generator may be used to control fluid injection, e.g., which may act synergistically or even act in opposing ways, depending on the application.

In one aspect, the present invention is generally directed to applying acoustic waves, such as surface acoustic waves, to a fluid flowing in a channel, such as a microfluidic channel. A surface acoustic wave ("SAW") is, generally speaking, an acoustic wave able to travel along the surface of a material exhibiting elasticity, with an amplitude that typically decays exponentially with depth into the material. By selecting suitable acoustic waves, pressure changes may be induced in the fluid, which can be used to manipulate the fluid in some cases. For example, acoustic waves applied to a fluid may increase or decrease the pressure on the fluid, which may affect the position of a fluidic interface between the fluid and another fluid. In some cases, the interface may be disrupted upon application of the acoustic waves, which may cause the interface to break or allow fluid mixing to occur.

The acoustic waves may be applied at varying amplitudes or powers in some cases. In some cases, the pressure changes created in the fluid may be a function of the power of the acoustic wave. For example, the acoustic wave may have a power of at least about 0 dBm, at least about 3 dBm, at least about 6 dBm, at least about 9 dBm, at least about 12 dBm, at least about 15 dBm, at least about 20 dBM, etc. The surface acoustic wave may also have any suitable average frequency, in various embodiments. For example, the average frequency of the surface acoustic wave may be between about 100 MHz and about 200 MHz, between about 130 MHz and about 160 MHz, between about 140 MHz and about 150 MHz, between about 100 MHz and about 120 MHz, between about 120 MHz and about 140 MHz, between about 140 MHz and about 160 MHz, between about 160 MHz and about 180 MHz, or between about 180 MHz and about 200 MHz or the like, and/or combinations thereof. In other embodiments, the frequency may be between about 50 Hz and about 100 KHz, between about 100 Hz and about 2 kHz, between about 100 Hz and about 1,000 Hz, between about 1,000 Hz and about 10,000 Hz, between about 10,000 Hz and about 100,000 Hz, or the like, and/or combinations thereof. In some cases, the frequency may be at least about 10 Hz, at least about 30 Hz, at least about 50 Hz, at least about 100 Hz, at least about 300 Hz, at least about 1,000 Hz, at least about 3,000 Hz, at least about 10,000 Hz, at least about 30,000 Hz, at least about 100,000 Hz, at least about 300,000 Hz, at least about 1 MHz, at least about 3 MHz, at least about 10 MHz, at least about 30 MHz, at least about 100 MHz, at least about 300 MHz, or at least about 1 GHz or more in some embodiments. In certain instances, the frequency may be no more than about 1 GHz, no more than about 300 MHz, no more than about 100 MHz, no more than about 30 MHz, no more than about 10 MHz, no more than about 3 MHz, no more than about 1 MHz, no more than about 300,000 Hz, no more than about 100,000 Hz, no more than about 30,000 Hz, no more than about 10,000 Hz, no more than about 3,000 Hz, no more than about 1,000 Hz, no more than about 300 Hz, no more than about 100 Hz, or the like. Combinations of any of the above frequencies and/or other frequencies are also possible in some cases.

The acoustic waves may be applied at any suitable direction to the fluid, e.g., at an interface or junction. In some embodiments, acoustic waves may be applied orthogonally, or in a downstream direction or an upstream direction, relative to the flow of fluid in a channel. For example, acoustic waves may be applied to a channel, such as a microfluidic channel, in a direction of fluid flow within the channel, in a direction opposite of fluid flow within the channel, or in another direction (e.g., perpendicular to fluid flow within the channel). In other embodiments, the acoustic waves may be applied at any suitable angle relative to the microfluidic channel, for example, about 0°, about 5°, about 10°, about 20°, about 30°, about 40°, about 50°, about 60°, about 70°, about 80°, about 90°, about 100°, about 110°, about 120°, about 130°, about 140°, about 150°, about 160°, about 170°, about 175°, about 180° etc. In some cases, more than one acoustic wave may be applied to control fluid flow within the channel. The acoustic waves may be applied at the same, or different regions of a channel, depending on the application. For instance, in some cases, a first acoustic wave and a second acoustic wave may be applied to overlapping portions of a fluid, e.g., at an interface or a junction, or a first acoustic wave may be applied to a first portion of a fluid within a channel, and the second acoustic wave may be applied to a second portion of the fluid within the channel. If more than one acoustic wave is applied to a fluid, the acoustic waves may be applied in any suitable order, e.g., simultaneously, sequentially, periodically, etc.

Without wishing to be bound by any theory, it should be noted that acoustic waves may be very rapidly controlled, e.g., electrically, and typically can be applied to fluids at very small time scales. Thus, individual regions of fluids, e.g., droplets of fluid as is discussed herein, may be controlled to an arbitrary degree, e.g., without affecting other regions or droplets of fluids, even nearby or adjacent ones. For example, an acoustic wave may be applied to a first region or droplet, then no acoustic wave may be applied, or an acoustic wave of a different magnitude and/or frequency, applied to an adjacent or nearby second region or droplet. Thus, each region or droplet can be independently controlled, without affecting adjacent or nearby regions or droplets. In contrast, in other microfluidic systems, such a high per-region or per-droplet basis for control of fluid or droplet characteristics cannot typically be achieved.

In addition, in some cases, the acoustic waves may be applied continuously, or intermittently or "pulsed." In some cases, the acoustic waves may be intermittently applied at a frequency, or in a way, such that individual droplets or regions are affected by the acoustic waves, but other droplets or regions are not. In addition, in some cases, the acoustic waves may be constant (i.e., having a fixed magnitude), or the acoustic wave may have an amplitude whose magnitude varies in time, e.g., the acoustic wave may have an amplitude that varies independently of the frequency of the acoustic wave.

As discussed, the acoustic waves may be applied to any suitable channel. In one set of embodiments, the acoustic waves are applied to a fluid contained within a channel, such as a microfluidic channel, to control the fluid. Various examples of microfluidic channels are discussed herein. More than one fluid may be present within the channel, in some instances, e.g., flowing as separate phases (for example, side-by-side, as droplets of a first fluid contained within a second fluid, etc.). As discussed herein, non-limiting examples of such channels include straight channels, bent channels, droplet-making channel configurations, and the like.

In some embodiments, the width of the channel may be chosen such that it is no more than about the full width at half maximum (FWHM) or 90% of the maximum of the acoustic wave or acoustic wave front. Without wishing to be bound by any theory, it is believed that such dimensions of the channel, relative to the acoustic wave or acoustic wave front, may decrease flow vortices that may be formed, which may decrease efficiency.

In some cases, the surface acoustic waves may be created using a surface acoustic wave generator such as an interdigitated transducer, and/or a material such as a piezoelectric substrate. The piezoelectric substrate may be isolated from the substrate except at or proximate the location where the acoustic waves are to be applied, e.g., proximate a first or second channel, proximate a junction of two or more channels, etc. At such locations, the substrate may be coupled to the piezoelectric substrate (or other material) by one or more coupling regions.

Any suitable technique may be used to create a surface acoustic wave, in various aspects of the invention. In some cases, the surface acoustic waves may be created using a surface acoustic wave generator such as an interdigitated transducer, and/or a material such as a piezoelectric substrate. The piezoelectric substrate may be isolated from the substrate except at or proximate the location where the acoustic waves are to be applied, e.g., proximate a first or second channel, proximate a junction of two or more channels, etc. At such locations, the substrate may be coupled to the piezoelectric substrate (or other material) by one or more coupling regions.

In some embodiments, the surface acoustic wave may be created by a generator attached to the surface of a material. In certain embodiments, the surface acoustic wave is created by using an interdigitated electrode or transducer able to convert electrical signals into acoustic waves able to travel along the surface of a material, and in some cases, the frequency of the surface acoustic waves may be controlled by controlling the spacing of the finger repeat distance of the interdigitated electrode or transducer. The surface acoustic waves can be formed on a piezoelectric substrate or other material that may be coupled to a microfluidic substrate at specific locations, e.g., at locations within the microfluidic substrate where injection or mixing is to take place. Suitable voltages (e.g., sinusoidal or other periodically varying voltages) are applied to the piezoelectric substrate, which converts the electrical signals into mechanical vibrations, i.e., surface acoustic waves or sound. The sound is then coupled to the microfluidic substrate, e.g., from the surface of the material. In the microfluidic substrate, the vibrations pass into liquid within microfluidic channels in the microfluidic substrate (e.g., to a liquid containing droplets), which give rise to internal streaming within the fluid. Thus, by controlling the applied voltage, streaming within the microfluidic channel may be controlled, which may be used to control droplets within the microfluidic channel, e.g., to cause fluid injection or mixing to occur.

Figure 3:
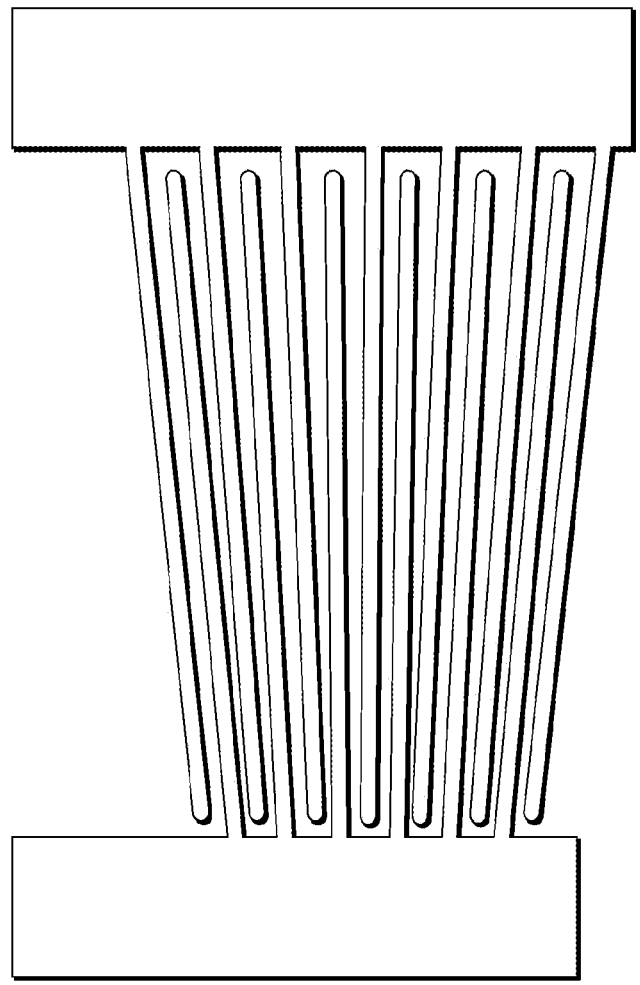
FIG. 3 illustrates a tapered interdigitated transducer for use in some embodiments of the invention.

An interdigitated transducer typically comprises one, two, or more electrodes containing a plurality of "fingers" extending away from the electrode, wherein at least some of the fingers are interdigitated. The fingers may be of any length, and may independently have the same or different lengths. The fingers may be spaced on the transducer regularly or irregularly. In some cases, the fingers may be substantially parallel, although in other embodiments they need not be substantially parallel. For example, in one set of embodiments, the interdigitated transducer is a tapered interdigitated transducer. In some cases, the fingers in a tapered interdigitated transducer may be arranged such that the fingers are angled inwardly, e.g., as shown in FIG. 3. Examples of such transducers may be found, e.g., in International Patent Application No. PCT/US2011/048804, filed Aug. 23, 2011, entitled "Acoustic Waves in Microfluidics," by Weitz, et al., published as WO 2012/027366 on Mar. 1, 2012; and International Patent Application No. PCT/US2013/047829, filed Jun. 26, 2013, entitled "Control of Entities Such as Droplets and Cells Using Acoustic Waves," by Weitz, et al., published as WO 2014/004630 on Jan. 3, 2014, each incorporated herein by reference in their entireties.

The interdigitated electrode typically includes of two interlocking comb-shaped metallic electrodes that do not touch, but are interdigitated. The electrodes may be formed from any suitable electrode material, for example, metals such as gold, silver, copper, nickel, or the like. The operating frequency of the interdigitated electrode may be determined, in some embodiments, by the ratio of the sound velocity in the substrate to twice the finger spacing. For instance, in one set of embodiments, the finger repeat distance may be between about 10 micrometers and about 40 micrometers, between about 10 micrometers and about 30 micrometers, between about 20 micrometers and about 40 micrometers, between about 20 micrometers and about 30 micrometers, or between about 23 micrometers and about 28 micrometers.

The interdigitated electrode may be positioned on a piezoelectric substrate, or other material able to transmit surface acoustic waves, e.g., to a coupling region. The piezoelectric substrate may be formed out of any suitable piezoelectric material, for example, quartz, lithium niobate, lithium tantalate, lanthanum gallium silicate, etc. In one set of embodiments, the piezoelectric substrate is anisotropic, and in some embodiments, the piezoelectric substrate is a Y-cut $LiNbO_3$ material.

The piezoelectric substrate may be activated by any suitable electronic input signal or voltage to the piezoelectric substrate (or portion thereof). For example, the input signal may be one in which a periodically varying signal is used, e.g., to create corresponding acoustic waves. For instance, the signals may be sine waves, square waves, sawtooth waves, triangular waves, or the like. The frequency may be for example, between about 50 Hz and about 100 KHz, between about 100 Hz and about 2 kHz, between about 100 Hz and about 1,000 Hz, between about 1,000 Hz and about 10,000 Hz, between about 10,000 Hz and about 100,000 Hz, or the like, and/or combinations thereof. In some cases, the frequency may be at least about 50 Hz, at least about 100 Hz, at least about 300 Hz, at least about 1,000 Hz, at least about 3,000 Hz, at least about 10,000 Hz, at least about 30,000 Hz, at least about 100,000 Hz, at least about 300,000 Hz, at least about 1 MHz, at least about 3 MHz, at least about 10 MHz, at least about 30 MHz, at least about 100 MHz, at least about 300 MHz, or at least about 1 GHz or more in some embodiments. In certain instances, the frequency may be no more than about 1 GHz, no more than about 300 MHz, no more than about 100 MHz, no more than about 30 MHz, no more than about 10 MHz, no more than about 3 MHz, no more than about 1 MHz, no more than about 300,000 Hz, no more than about 100,000 Hz, no more than about 30,000 Hz, no more than about 10,000 Hz, no more than about 3,000 Hz, no more than about 1,000 Hz, no more than about 300 Hz, no more than about 100 Hz, or the like.

The interdigitated electrode may be positioned on the piezoelectric substrate (or other suitable material) such that acoustic waves produced by the interdigitated electrodes are directed at a region of acoustic coupling between the piezoelectric substrate and the microfluidic substrate. For example, the piezoelectric substrate and the microfluidic substrate may be coupled or physically bonded to each other, for example, using ozone plasma treatment, or other suitable techniques. In some cases, the rest of the piezoelectric substrate and the microfluidic substrate are at least acoustically isolated from each other, and in certain embodiments, the piezoelectric substrate and the microfluidic substrate are physically isolated from each other. Without wishing to be bound by any theory, it is believed that due to the isolation, acoustic waves created by the interdigitated electrode and the piezoelectric substrate do not affect the microfluidic substrate except at regions where it is desired that the acoustic waves are applied, e.g., at a channel or a junction.

The coupling region may have any suitable shape and/or size. The coupling region may be round, oval, or have other shapes, depending on the embodiment. In some cases, two, three, or more coupling regions may be used. In one set of embodiments, the coupling region is sized to be contained within a microfluidic channel. In other embodiments, however, the coupling region may be larger. The coupling region may be positioned within a channel or proximate to the channel, in some embodiments.

In some cases, control of the droplets into one of the channels may be achieved by using a tapered interdigitated transducer. A tapered interdigitated transducer may allow relatively high control of the location at which a SAW is applied to a channel, in contrast to an interdigitated transducer where all of the fingers are parallel to each other and the spacing between electrodes is constant. Without wishing to be bound by any theory, it is believed that the location which a SAW can be applied by an interdigitated transducer is controlled, at least in part, by the spacing between the electrodes. By controlling the potential applied to the interdigitated transducer, and thereby controlling the resonance frequency of the applied SAW, the position and/or the strength of the SAW as applied by the interdigitated transducer may be correspondingly controlled. Thus, for example, applying a first voltage to an interdigitated transducer may cause a first resonance frequency of the resulting SAW to be applied (e.g., within a channel), while applying a second voltage may cause a second resonance frequency of the resulting SAW to be applied to a different location (e.g., within the channel). As another example, a plurality of coupling regions may be used, e.g., in combination with one or more tapered interdigitated transducers.

The microfluidic substrate may be any suitable substrate which contains or defines one or more microfluidic channels. For instance, as is discussed below, the microfluidic substrate may be formed out of polydimethylsiloxane, polytetrafluoroethylene, or other suitable elastomeric polymers, at least according to various non-limiting examples.

Other examples of the production of droplets of fluid surrounded by a liquid are described in International Patent Application Serial No. PCT/US2004/010903, filed Apr. 9, 2004 by Link, et al. and International Patent Application Serial No. PCT/US03/20542, filed Jun. 30, 2003 by Stone, et al., published as WO 2004/002627 on Jan. 8, 2004, each incorporated herein by reference. In various embodiments, acoustic waves may be applied to such systems.

As mentioned, some aspects of the present invention relate to the injection of fluids into droplets, for example, in microfluidic systems. In some cases, relatively small amounts of fluid may be injected or added to a droplet. For instance, the volume injected may be less than about 10 microliters, less than about 1 microliter, less than about 100 nanoliters, less than about 10 nanoliters, less than about 1 nanoliter, less than about 100 picoliters, less than about 10 picoliters, less than about 1 picoliter, etc. In some cases, fluid may be injected while the fluid in the first channel is in motion (i.e., flowing through a channel). In other cases, fluid may be injected while the fluid in the channel is held stationary. For example, pressure in the first channel may be controlled such that a droplet is urged to an intersection between the first channel and a second channel. The pressure and/or fluid flow within the first channel may then be decreased such that the droplet is then held stationary at the intersection, thereby allowing a desired amount of fluid to be injected into the droplet. The pressure may then be increased and/or fluid flow may be controlled to urge the droplet away from the intersection once a desired amount of fluid has been transported.

In some instances, the second channel may be configured, e.g., with a pump or other pressure control device such that fluid can be forcibly injected from the first channel, e.g., to a fluidic droplet, for example, without reliance on a difference in radii of curvature of the interface, or the like.

The flow velocity of the fluidic droplet within the first channel may be determined in some embodiments by factors such as the pressure or the pressure difference between the fluidic droplet in the first channel and the fluid in the second channel, the fluid pressure in one or both channels, the size of the orifice between the first channel and the second channel, the angle of intersection between the first and second channels, etc., e.g., as discussed above. The fluid pressure may be controlled using any suitable technique, for example, using a pump, siphon pressure, acoustic waves, or the like.

As mentioned, the volume of fluid injected may be controlled using any suitable technique, for example, by controlling the frequency, duration, intensity, timing, angle, etc. of acoustic waves applied to the interface. For instance, in some embodiments, the flow rate of fluid in the first channel can be used to control the volume of fluid injected and/or withdrawn. It is believed that this can be controlled since the flow rate of fluid in the first channel controls the flow rate of fluidic droplets in the first channel, which thereby controls the amount of time that the fluidic droplets are present at the intersection and/or exposed to fluid in the second channel.

In some embodiments, the volume of fluid exchanged between two fluids may be controlled by controlling the residence time of a first fluid in proximity to a second fluid, e.g., by controlling the residence time of a fluid in the first channel and positioned in front of a second channel. As a non-limiting example, the residence time of a fluidic in a droplet in the first channel positioned in front of the second channel may be controlled by varying the flow rate of fluid in the first channel. That is, a longer residence time may be achieved by slowing the flow rate or even stopping the flow of the fluid in the first channel, relative to the second channel. Likewise, a shorter residence time may be achieved by increasing the flow rate of the fluid in the first channel.

In another set of embodiments, the duration of the acoustic waves, e.g., while a droplet is positioned in an intersection of first and second channels may by varied. For example, to allow more fluid to exchange between fluid in the first channel and in the second channel, the interface may be disrupted for a longer period of time. To allow a smaller amount of fluid exchange, the interface may be disrupted for a shorter period of time.

Thus, in some embodiments, fluid may be injected into a fluidic channel, e.g., in a fluidic droplet contained within the channel, which may in some cases cause mixing of the injected fluid with other fluids within the fluidic droplet to occur. It should be understood that, in some embodiments involving the injection of a fluid from a second channel into a first channel, the fluid that is injected may be injected into a droplet contained within the first channel and/or into fluid contained within the first channel, e.g., forming a new droplet. Thus, in some embodiments, fluid injection using a first channel and a second channel as discussed herein may be used to create new droplets of a fluid from the second channel that are individually contained within fluid within the first channel. In addition, as discussed, other configurations of two or more channels may be used in addition to, or instead of, the T-junction shown in FIG. 1.

For example, in one set of embodiments, the fluid may be injected into the fluidic droplet using a needle such as a microneedle, a nozzle, an orifice, a tube, or other such devices. In another set of embodiments, the fluid may be injected directly into a fluidic droplet using a fluidic channel as the fluidic droplet comes into contact with the fluidic channel. For instance, in certain embodiments, a first channel containing a fluid may be intersected by a second channel at an intersection. Fluid from the second channel may be injected into the first channel, for example, using acoustic waves. For example, when a droplet contained within the first channel passes through the intersection, fluid from the second channel may be urged into the intersection, thereby entering the droplet and causing injection of fluid from the second channel into the droplet to occur.

It should be noted that, since this process may be controlled electronically, rapid droplet injection may be achieved in some cases, e.g., using suitable acoustic waves. For instance, at least about 10 droplets per second may be injected in some cases, and in other cases, at least about 20 droplets per second, at least about 30 droplets per second, at least about 100 droplets per second, at least about 200 droplets per second, at least about 300 droplets per second, at least about 500 droplets per second, at least about 750 droplets per second, at least about 1000 droplets per second, at least about 1500 droplets per second, at least about 2000 droplets per second, at least about 3000 droplets per second, at least about 5000 droplets per second, at least about 7500 droplets per second, at least about 10,000 droplets per second or more droplets per second may be created in such a fashion.

In some cases, the magnitude of the pressure change, e.g., at an interface, is related to the power or the amplitude of the applied acoustic waves. In certain embodiments, the acoustic waves may be applied at an amplitude and/or at a direction selected to alter a flow characteristic of the fluid, e.g., its flow rate or direction of flow. For instance, in one set of embodiments, droplets of a first fluid may be formed within a second fluid, and the acoustic waves may be applied to alter the formation of the droplets, e.g., altering the rate of creation of droplets, the volume of the droplets, etc.

In some embodiments, the droplets and/or the injected fluids may contain cells or other species. In some cases, a fluid to be injected into a droplet may contain a species that is desired to be injected into the droplet, e.g., an injected fluid may be used to add a species to a droplet. Examples of species include, but are not limited to, a chemical, biochemical, or biological entity, a cell, a particle, a bead, gases, molecules, a pharmaceutical agent, a drug, DNA, RNA, proteins, a fragrance, a reactive agent, a biocide, a fungicide, a pesticide, a preservative, or the like. Thus, the species can be any substance that can be contained in a fluid and can be differentiated from the fluid containing the species. For example, the species may be dissolved or suspended in the fluid. The species may be present in one or more of the fluids. If the fluids contain droplets, the species can be present in some or all of the droplets. Additional non-limiting examples of species that may be present include, for example, biochemical species such as nucleic acids such as siRNA, RNAi and DNA, proteins, peptides, or enzymes. Still other examples of species include, but are not limited to, nanoparticles, quantum dots, fragrances, proteins, indicators, dyes, fluorescent species, chemicals, or the like. As yet another example, the species may be a drug, pharmaceutical agent, or other species that has a physiological effect when ingested or otherwise introduced into the body, e.g., to treat a disease, relieve a symptom, or the like. In some embodiments, the drug may be a small-molecule drug, e.g., having a molecular weight of less than about 1000 Da or less than about 2000 Da.

In some embodiments, the droplets are relatively monodisperse, or the droplets may have relatively uniform cross-sectional diameters in certain embodiments. In some embodiments, the droplets may have an overall average diameter and a distribution of diameters such that no more than about 5%, no more than about 2%, or no more than about 1% of the particles or droplets have a diameter less than about 90% (or less than about 95%, or less than about 99%) and/or greater than about 110% (or greater than about 105%, or greater than about 101%) of the overall average diameter of the plurality of droplets.

In some embodiments, the droplets may have an average diameter of, for example, less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers in some cases. The average diameter may also be at least about 1 micrometer, at least about 2 micrometers, at least about 3 micrometers, at least about 5 micrometers, at least about 10 micrometers, at least about 15 micrometers, or at least about 20 micrometers in certain cases. In some cases combinations of these are also possible, e.g., the droplets may have an average diameter of between about 1 micrometer and about 1 mm. The "average diameter" of a plurality or series of droplets is the arithmetic average of the average diameters of each of the droplets. Those of ordinary skill in the art will be able to determine the average diameter (or other characteristic dimension) of a plurality or series of droplets, for example, using laser light scattering, microscopic examination, or other known techniques. The diameter of a droplet, in a non-spherical droplet, may be taken as the diameter of a perfect sphere having the same volume as the droplet.

In some embodiments, a first fluid may be more hydrophilic (or more hydrophobic) relative to a second fluid, and the first and the second fluids may be substantially immiscible. Thus, the first fluid can from a discrete droplet within the second fluid (or vice versa), e.g., without substantial mixing of the first fluid and the second fluid (although some degree of mixing may nevertheless occur under some conditions). In some embodiments, two fluids are immiscible, or not miscible, with each other when one is not soluble in the other to a level of at least 10% by weight at the temperature and under the conditions at which the droplets are produced. For instance, two fluids may be selected to be immiscible within the time frame of the formation of the fluidic droplets within the other fluid. In some cases, a first fluid is hydrophilic while another fluid is hydrophobic or immiscible with the first fluid. Examples of hydrophilic liquids include, but are not limited to, water and other aqueous solutions comprising water, such as cell or biological media, ethanol, salt solutions, etc. Examples of hydrophobic liquids include, but are not limited to, oils such as hydrocarbons, silicon oils, fluorocarbon oils, organic solvents etc.

In certain aspects of the invention, sensors are provided that can sense and/or determine one or more characteristics of the fluidic droplets, and/or a characteristic of a portion of the fluidic system containing the fluidic droplet (e.g., the liquid surrounding the fluidic droplet) in such a manner as to allow the determination of one or more characteristics of the fluidic droplets. Characteristics determinable with respect to the droplet and usable in the invention can be identified by those of ordinary skill in the art. Non-limiting examples of such characteristics include fluorescence, spectroscopy (e.g., optical, infrared, ultraviolet, etc.), radioactivity, mass, volume, density, temperature, viscosity, pH, concentration of a substance, such as a biological substance (e.g., a protein, a nucleic acid, etc.), or the like. Thus, for example, a plurality of droplets may be determined using sensors, and those droplets having (or missing) certain characteristics may be selected for injection of a fluid.

A variety of definitions are now provided which will aid in understanding various aspects of the invention. Following, and interspersed with these definitions, is further disclosure that will more fully describe the invention.

As noted, various embodiments of the present invention relate to droplets of fluid surrounded by a liquid (e.g., suspended). The droplets may be of substantially the same shape and/or size, or of different shapes and/or sizes, depending on the particular application. As used herein, the term "fluid" generally refers to a substance that tends to flow and to conform to the outline of its container, i.e., a liquid, a gas, a viscoelastic fluid, etc. Typically, fluids are materials that are unable to withstand a static shear stress, and when a shear stress is applied, the fluid experiences a continuing and permanent distortion. The fluid may have any suitable viscosity that permits flow. If two or more fluids are present, each fluid may be independently selected among essentially any fluids (liquids, gases, and the like) by those of ordinary skill in the art, by considering the relationship between the fluids. The fluids may each be miscible or immiscible. For example, two fluids can be selected to be essentially immiscible within the time frame of formation of a stream of fluids, or within the time frame of reaction or interaction. Where the portions remain liquid for a significant period of time, then the fluids should be essentially immiscible. Where, after contact and/or formation, the dispersed portions are quickly hardened by polymerization or the like, the fluids need not be as immiscible. Those of ordinary skill in the art can select suitable miscible or immiscible fluids, using contact angle measurements or the like, to carry out the techniques of the invention.

As used herein, a first entity is "surrounded" by a second entity if a closed planar loop can be drawn around the first entity through only the second entity. A first entity is "completely surrounded" if closed loops going through only the second entity can be drawn around the first entity regardless of direction (orientation of the loop). In one embodiment, the first entity is a cell, for example, a cell suspended in media is surrounded by the media. In another embodiment, the first entity is a particle. In yet another embodiment, the first entity is a fluid. The second entity may also be a fluid in some cases (e.g., as in a suspension, an emulsion, etc.), for example, a hydrophilic liquid may be suspended in a hydrophobic liquid, a hydrophobic liquid may be suspended in a hydrophilic liquid, a gas bubble may be suspended in a liquid, etc. Typically, a hydrophobic liquid and a hydrophilic liquid are essentially immiscible with respect to each other, where the hydrophilic liquid has a greater affinity to water than does the hydrophobic liquid. Examples of hydrophilic liquids include, but are not limited to, water and other aqueous solutions comprising water, such as cell or biological media, salt solutions, etc., as well as other hydrophilic liquids such as ethanol. Examples of hydrophobic liquids include, but are not limited to, oils such as hydrocarbons, silicone oils, mineral oils, fluorocarbon oils, organic solvents etc. Other examples of suitable fluids, including hydrophobic and hydrophilic liquids, have been previously described.

Similarly, a "droplet," as used herein, is an isolated portion of a first fluid that is completely surrounded by a second fluid. It is to be noted that a droplet is not necessarily spherical, but may assume other shapes as well, for example, depending on the external environment. In one embodiment, the droplet has a minimum cross-sectional dimension that is substantially equal to the largest dimension of the channel perpendicular to fluid flow in which the droplet is located.

As mentioned, in some, but not all embodiments, the systems and methods described herein may include one or more microfluidic components, for example, one or more microfluidic channels. "Microfluidic," as used herein, refers to a device, apparatus or system including at least one fluid channel having a cross-sectional dimension of less than 1 mm, and a ratio of length to largest cross-sectional dimension of at least 3:1. A "microfluidic channel," as used herein, is a channel meeting these criteria. The "cross-sectional dimension" of the channel is measured perpendicular to the direction of fluid flow within the channel. Thus, some or all of the fluid channels in microfluidic embodiments of the invention may have maximum cross-sectional dimensions less than 2 mm, and in certain cases, less than 1 mm. In one set of embodiments, all fluid channels containing embodiments of the invention are microfluidic or have a largest cross sectional dimension of no more than 2 mm or 1 mm. In certain embodiments, the fluid channels may be formed in part by a single component (e.g. an etched substrate or molded unit). Of course, larger channels, tubes, chambers, reservoirs, etc. can be used to store fluids and/or deliver fluids to various components or systems of the invention. In one set of embodiments, the maximum cross-sectional dimension of the channel(s) containing embodiments of the invention is less than 500 microns, less than 200 microns, less than 100 microns, less than 50 microns, or less than 25 microns.

A "channel," as used herein, means a feature on or in an article (substrate) that at least partially directs flow of a fluid. The channel can have any cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and/or outlet(s). A channel may also have an aspect ratio (length to average cross sectional dimension) of at least 2:1, more typically at least 3:1, 5:1, 10:1, 15:1, 20:1, or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (i.e., a concave or convex meniscus).

The channel may be of any size, for example, having a largest dimension perpendicular to fluid flow of less than about 5 mm or 2 mm, or less than about 1 mm, or less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm. In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, positioned to intersect with each other, etc.

In one set of embodiments, the fluidic droplets may contain cells or other entities, such as proteins, viruses, macromolecules, particles, etc. As used herein, a "cell" is given its ordinary meaning as used in biology. The cell may be any cell or cell type. For example, the cell may be a bacterium or other single-cell organism, a plant cell, or an animal cell. If the cell is a single-cell organism, then the cell may be, for example, a protozoan, a trypanosome, an amoeba, a yeast cell, algae, etc. If the cell is an animal cell, the cell may be, for example, an invertebrate cell (e.g., a cell from a fruit fly), a fish cell (e.g., a zebrafish cell), an amphibian cell (e.g., a frog cell), a reptile cell, a bird cell, or a mammalian cell such as a primate cell, a bovine cell, a horse cell, a porcine cell, a goat cell, a dog cell, a cat cell, or a cell from a rodent such as a rat or a mouse. If the cell is from a multicellular organism, the cell may be from any part of the organism. For instance, if the cell is from an animal, the cell may be a cardiac cell, a fibroblast, a keratinocyte, a heptaocyte, a chondracyte, a neural cell, a osteocyte, a muscle cell, a blood cell, an endothelial cell, an immune cell (e.g., a T-cell, a B-cell, a macrophage, a neutrophil, a basophil, a mast cell, an eosinophil), a stem cell, etc. In some cases, the cell may be a genetically engineered cell. In certain embodiments, the cell may be a Chinese hamster ovarian ("CHO") cell or a 3T3 cell.

A variety of materials and methods, according to certain aspects of the invention, can be used to form any of the above-described components of the systems and devices of the invention. In some cases, the various materials selected lend themselves to various methods. For example, various components of the invention can be formed from solid materials, in which the channels can be formed via micromachining, film deposition processes such as spin coating and chemical vapor deposition, laser fabrication, photolithographic techniques, etching methods including wet chemical or plasma processes, and the like. See, for example, Scientific American, 248:44-55, 1983 (Angell, et al). In one embodiment, at least a portion of the fluidic system is formed of silicon by etching features in a silicon chip. Technologies for precise and efficient fabrication of various fluidic systems and devices of the invention from silicon are known. In another embodiment, various components of the systems and devices of the invention can be formed of a polymer, for example, an elastomeric polymer such as polydimethylsiloxane ("PDMS"), polytetrafluoroethylene ("PTFE" or Teflon®), or the like.

Different components can be fabricated of different materials. For example, a base portion including a bottom wall and side walls can be fabricated from an opaque material such as silicon or PDMS, and a top portion can be fabricated from a transparent or at least partially transparent material, such as glass or a transparent polymer, for observation and/or control of the fluidic process. Components can be coated so as to expose a desired chemical functionality to fluids that contact interior channel walls, where the base supporting material does not have a precise, desired functionality. For example, components can be fabricated as illustrated, with interior channel walls coated with another material. Material used to fabricate various components of the systems and devices of the invention, e.g., materials used to coat interior walls of fluid channels, may desirably be selected from among those materials that will not adversely affect or be affected by fluid flowing through the fluidic system, e.g., material(s) that is chemically inert in the presence of fluids to be used within the device.

In one embodiment, various components of the invention are fabricated from polymeric and/or flexible and/or elastomeric materials, and can be conveniently formed of a hardenable fluid, facilitating fabrication via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, or mixture of such polymers heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, etc.

Silicone polymers are preferred in one set of embodiments, for example, the silicone elastomer polydimethylsiloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying fabrication of the microfluidic structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures of the invention from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, components can be fabricated and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in an article entitled "Rapid Prototyping of Microfluidic Systems and Polydimethylsiloxane," Anal. Chem., 70:474-480, 1998 (Duffy et al.), incorporated herein by reference.

Another advantage to forming microfluidic structures of the invention (or interior, fluid-contacting surfaces) from oxidized silicone polymers is that these surfaces can be much more hydrophilic than the surfaces of typical elastomeric polymers (where a hydrophilic interior surface is desired). Such hydrophilic channel surfaces can thus be more easily filled and wetted with aqueous solutions than can structures comprised of typical, unoxidized elastomeric polymers or other hydrophobic materials.

In one embodiment, a bottom wall is formed of a material different from one or more side walls or a top wall, or other components. For example, the interior surface of a bottom wall can comprise the surface of a silicon wafer or microchip, or other substrate. Other components can, as described above, be sealed to such alternative substrates. Where it is desired to seal a component comprising a silicone polymer (e.g. PDMS) to a substrate (bottom wall) of different material, the substrate may be selected from the group of materials to which oxidized silicone polymer is able to irreversibly seal (e.g., glass, silicon, silicon oxide, quartz, silicon nitride, polyethylene, polystyrene, epoxy polymers, and glassy carbon surfaces which have been oxidized). Alternatively, other sealing techniques can be used, as would be apparent to those of ordinary skill in the art, including, but not limited to, the use of separate adhesives, thermal bonding, solvent bonding, ultrasonic welding, etc.

The following documents are incorporated herein by reference in their entireties: International Patent Application No. PCT/US2011/048804, filed Aug. 23, 2011, entitled "Acoustic Waves in Microfluidics," by Weitz, et al., published as WO 2012/027366 on Mar. 1, 2012; International Patent Application No. PCT/US2013/047829, filed Jun. 26, 2013, entitled "Control of Entities Such as Droplets and Cells Using Acoustic Waves," by Weitz, et al., published as WO 2014/004630 on Jan. 3, 2014; and International Patent Application No. PCT/US2013/066591, filed Oct. 24, 2013, entitled "Systems and Methods for Droplet Production and Manipulation Using Acoustic Waves," by Weitz, et al., published as WO 2014/066624 on May 1, 2014.

In addition, the following documents are incorporated herein by reference: U.S. patent application Ser. No. 11/360,845, filed Feb. 23, 2006, entitled "Electronic Control of Fluidic Species," by Link, et al., published as U.S. Patent Application Publication No. 2007/0003442 on Jan. 4, 2007; U.S. patent application Ser. No. 08/131,841, filed Oct. 4, 1993, entitled "Formation of Microstamped Patterns on Surfaces and Derivative Articles," by Kumar, et al., now U.S. Pat. No. 5,512,131, issued Apr. 30, 1996; priority to International Patent Application No. PCT/US96/03073, filed Mar. 1, 1996, entitled "Microcontact Printing on Surfaces and Derivative Articles," by Whitesides, et al., published as WO 96/29629 on Jun. 26, 1996; U.S. patent application Ser. No. 09/004,583, filed Jan. 8, 1998, entitled "Method of Forming Articles Including Waveguides via Capillary Micromolding and Microtransfer Molding," by Kim, et al., now U.S. Pat. No. 6,355,198, issued Mar. 12, 2002; International Patent Application No. PCT/US01/16973, filed May 25, 2001, entitled "Microfluidic Systems including Three-Dimensionally Arrayed Channel Networks," by Anderson, et al., published as WO 01/89787 on Nov. 29, 2001; U.S. Provisional Patent Application Ser. No. 60/392,195, filed Jun. 28, 2002, entitled "Multiphase Microfluidic System and Method," by Stone, et al.; U.S. Provisional Patent Application Ser. No. 60/424,042, filed Nov. 5, 2002, entitled "Method and Apparatus for Fluid Dispersion," by Link, et al.; U.S. Provisional Patent Application Ser. No. 60/461,954, filed Apr. 10, 2003, entitled "Formation and Control of Fluidic Species," by Link, et al.; International Patent Application No. PCT/US03/20542, filed Jun. 30, 2003, entitled "Method and Apparatus for Fluid Dispersion," by Stone, et al., published as WO 2004/002627 on Jan. 8, 2004; U.S. Provisional Patent Application Ser. No. 60/498,091, filed Aug. 27, 2003, entitled "Electronic Control of Fluidic Species," by Link, et al.; International Patent Application No. PCT/US2004/010903, filed Apr. 9, 2004, entitled "Formation and Control of Fluidic Species," by Link, et al., published as WO 2004/091763 on Oct. 28, 2004; International Patent Application No. PCT/US2004/027912, filed Aug. 27, 2004, entitled "Electronic Control of Fluidic Species," by Link, et al., published as WO 2005/021151 on Mar. 10, 2005; U.S. patent application Ser. No. 11/024,228, filed Dec. 28, 2004, entitled "Method and Apparatus for Fluid Dispersion," by Stone, et al., published as U.S. Patent Application Publication No. 2005-0172476 on Aug. 11, 2005; U.S. Provisional Patent Application Ser. No. 60/659,045, filed Mar. 4, 2005, entitled "Method and Apparatus for Forming Multiple Emulsions," by Weitz, et al.; U.S. Provisional Patent Application Ser. No. 60/659,046, filed Mar. 4, 2005, entitled "Systems and Methods of Forming Particles," by Garstecki, et al.; and U.S. patent application Ser. No. 11/246,911, filed Oct. 7, 2005, entitled "Formation and Control of Fluidic Species," by Link, et al.

Also, U.S. Provisional Patent Application Ser. No. 62/017,301, filed Jun. 26, 2014, entitled "Fluid Injection Using Acoustic Waves," by Weitz, et al., is incorporated herein by reference in its entirety.

The following examples are intended to illustrate certain embodiments of the present invention, but do not exemplify the full scope of the invention.

EXAMPLE 1

This example illustrates that reactants can be added to drops that are used in droplet-based microfluidics. The injection in this example may be triggered on-demand by a pulse of a surface acoustic wave. A typical and simple setup is described below, but more complex operations are also possible.

The simple setup is a microfluidic PDMS (polydimethylsiloxane) channel that features a T-junction with two inlets and one outlet, as is shown in FIG. 1. A droplet emulsion enters through the "left arm" of the T-junction. The reactant to be added enters through the stem of the "T". Without the action of the SAW (surface acoustic wave), droplets simply pass the T-junction without any modification. In this "default mode" the interface between the reactant and the continuous phase of the droplet inlet is stationary and droplets do not touch the reactant phase. As a consequence no reactant is added to the drop. If acoustic actuation is triggered, for example by a signal of a detector that detects the light intensity of the drop, the interface may be deflected. In this "injection mode" a flowing drop touches the interface and the interface breaks up. As a result fluid of the reactant enters the drop.

The volume of the entering reactant is controlled by the acoustic pulse characteristics, such as pulse length and amplitude. In this way a desired amount of reactant can be added to the drop. In some cases, one or more IDTs (interdigited transducers) may be placed in such a way that the acoustics couples into one or more positions into the microfluidic channel. This can happen, for example, at the inlets and/or the outlets since only a relative change of pressure is necessary. In other words: increasing the inlet pressure may have a similar effect as decreasing the outlet pressure using IDTs in some cases. This control may be very fast with a very low relaxation time. In this way, a desired volume of a fluid can be added to each drop at the T-junction at high speed.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word "about" is used herein in reference to a number, it should be understood that still another embodiment of the invention includes that number not modified by the presence of the word "about."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method, comprising:
   providing a microfluidic system comprising a first microfluidic channel and a second microfluidic channel contacting the first microfluidic channel at a junction;
   providing a droplet of the first fluid contained by a carrying fluid in the first microfluidic channel, and a second fluid in the second microfluidic channel, wherein the first fluid and the second fluid contact each other at least partially within the junction to define a fluidic interface; and
   applying acoustic waves to the interface to urge the second fluid to flow into the droplet wherein, in the absence of the acoustic waves, the second fluid is not urged to enter the droplet.

2. The method of claim 1, wherein the acoustic waves are applied to at least a portion of the junction.

3. The method of claim 1, wherein the acoustic waves are applied to the first fluid in a direction of flow of the first fluid.

4. The method of claim 1, wherein the acoustic waves are applied to the first fluid opposite a direction of flow of the first fluid.

5. The method of claim 1, wherein the acoustic waves are applied to the second fluid in a direction of flow of the second fluid.

6. The method of claim 1, wherein the acoustic waves are applied to the second fluid opposite a direction of flow of the second fluid.

7. The method of claim 1, wherein the acoustic waves have a power of at least about 3 dBm.

8. The method of claim 1, wherein the acoustic waves have an average frequency of between about 430 MHz and about 160 MHz.

9. The method of claim 1, wherein the acoustic waves have an average frequency of between about 140 MHz and about 150 MHz.

10. The method of claim 1, further comprising applying pressure to the second fluid contained within the second microfluidic channel sufficient to cause at least a portion of the second fluid to enter the droplet of the first fluid.

11. The method of claim 1, wherein the first microfluidic channel and the second microfluidic channel from a T junction.

12. The method of claim 1, wherein the acoustic waves are generated by an acoustic wave generator.

13. The method of claim 12, wherein the acoustic wave generator comprises one or more interdigited transducers.

14. The method of claim 1, further comprising a second acoustic wave generator positioned to alter flow of fluid entering or leaving the junction.

15. The method of claim 1, wherein the microfluidic system comprises a piezoelectric substrate.

16. A method, comprising:
providing a microfluidic system comprising a first fluid contacting a second fluid at an interface separating the first fluid and the second fluid; and
applying acoustic waves to the interface, wherein the acoustic waves disrupt the interface to cause at least some mixing of the first fluid and the second fluid.

17. The method of claim 16, wherein the acoustic waves are applied to the first fluid in a direction of flow of the first fluid.

18. The method of claim 16, wherein the acoustic waves are applied to the second fluid in a direction of flow of the second fluid.

19. The method of claim 16, wherein the acoustic waves have a power of at least about 3 dBm.

20. The method of claim 16, wherein the acoustic waves are generated by an acoustic wave generator comprising one or more interdigited transducers.

* * * * *